United States Patent [19]

Bissinger

[11] 4,046,912

[45] Sept. 6, 1977

[54] S-P-METHOXYPHENYL N-2,3-DIBROMOPROPYLTHIOLCARBAMATE AND ITS USE IN THE CONTROL OF PLANT NEMATODES

[75] Inventor: William E. Bissinger, Akron, Ohio

[73] Assignee: PPG Industries, Inc., Pittsburgh, Pa.

[21] Appl. No.: 631,751

[22] Filed: Nov. 13, 1975

[51] Int. Cl.$^2$ .................. A01N 9/12; C07C 155/02
[52] U.S. Cl. ............................. 424/300; 260/455 A
[58] Field of Search .................. 260/455 A; 424/300

[56] References Cited

U.S. PATENT DOCUMENTS

| | | | |
|---|---|---|---|
| 3,046,189 | 7/1962 | Jacobi et al. | 424/300 |
| 3,075,875 | 1/1963 | Margot | 260/455 A X |
| 3,265,563 | 8/1966 | Yilles et al. | 424/300 |
| 3,846,467 | 11/1974 | Kudamatsu et al. | 260/45 TA |

*Primary Examiner*—Leonard Schenkman
*Attorney, Agent, or Firm*—Robert J. Grassi

[57] ABSTRACT

Disclosed is S-p-Methoxyphenyl N-2,3-dibromopropylthiolcarbamate which exhibits systemic control of the deleterious effects of nematodes upon plants, in particular systemic control of the deleterious effects of the Meloidogyne species, and foliar fungicidal activity against leaf rust of wheat.

14 Claims, No Drawings

S-P-METHOXYPHENYL N-2,3-DIBROMOPROPYLTHIOLCARBAMATE AND ITS USE IN THE CONTROL OF PLANT NEMATODES

BACKGROUND OF THE INVENTION

1. Field of the Invention

This invention concerns S-Substituted phenyl N-halogen substituted alkylthiolcarbamate, in particular, S-p-Methoxyphenyl N-2,3- dibromopropylthiolacarbamate, and the method of controlling the deleterious effects of nematodes by applying an effective amount of the compound to the vicinity of the infested area, particularly, to the foliage of the plant to control the deleterious effect of the nematodes upon the plant.

This invention also concerns the method of protecting plants against foliar fungus disease caused by fungus of the genera Puccinia and Phytophthorans, particularly, *Phytophthorans infestans* and Puccinia rubigo-vera.

2. Description of the Prior Art

Nematodes (nemas) attack plants (trees, shrubs, etc.) and plant parts such as stems, roots, and bulbs causing deleterious effects by weakening the plant, decreasing the yield of fruit, stunting its growth, or causing lesions through which other parasitic organisms enter and harm the plant.

One method of combatting nematodes living in the soil, or upon decaying vegatation is to rotate the crops, but this is ineffective when crops are growing. Another method is to use soil fungicides which kill nematodes, particularly those living in the soil, so as to rid the soil of these nematodes prior to crop planting. Examples of soil fungicides are methyl bromide, and chloropicrin. Soil fungicides are expensive, and in many cases are phytotoxic to plants. Another method is to apply nematocides to soil or to the bulbs to kill the nematodes prior to their entering the plant. Many nematodes, however, attack plants or become embedded within plants prior to application of the nematocide, or after the effective life of the nematocide, and these nematodes are not affected by such application of nematocides. Another method is to apply systemic nematocides, which are applied to the plant; e.g., the foliage of the plant, to systemically control the deleterious effect of nematodes on the plant. This systemic control may result either from one or several different mechanisms. It may result from a translocatin of the compound (or a metabolite thereof) from its application site (e.g., the foliage) to the area deleteriously affected by nematodes (the roots) where it controls the deleterious effect, e.g., by killing the nematodes or repelling them from the area, or by inducing rapid healing of the plant wound caused by the nematode. It may also result from a translocation of the compound (or a metabolite thereof) from the application site (foliage) through the plant to outside the area deleteriously affected by nematodes (e.g., the roots), where it provides a protective shield against nematodes, such as a root coating which repels or kills nematodes feeding upon this area of the plant. It may also result from the translocation of the compound or a metabolite thereof form its application site into the enzyme system of the plant where it stimulates formation of chemicals which repel or kill the nematodes attaching the plant or which rapidly heals the wounds caused by the nematodes.

Many thiolcarbamates are known as herbicides, fungicides, or nematocides, but very few are systemic nematocides. U.S. Pat. No. 2,977,209 and 3,265,563 disclose S-phenyl N-alkyl thiolcarbamates, S-chlorophenyl N-alkyl thiolcarbamates, S-ethyoxy N-allylthiolcarbamate, and S-ethoxy N-alkyl thiolcarbamates as herbicides and fungicides. U.S. Pat. No. 2,992,091 and U.S. Pat. No. 3,144,475 discloses S-substituted benzyl N,N-dialkylthiolcarbamates and dithiocarbamates as defoliants and herbicides. U.S. Pat. No. 3,632,332 discloses S-4-methylbenzyl-N,N-diethylthiocarbamate as a herbicide for rice fields. U.S. Pat. No. 3,301,885 discloses S-substituted phenyl N-alkyl, N-alkoxy thiolcarbamates as herbicides, miticides, and insecticides. U.S. Pat. No. 3,687,653 discloses trifluoromethylbenzyl N-alkyl thiolcarbamates as herbicides. U.S. Pat. No. 3,046,189 and Canadian Pat. No. 789,575 discloses S-alkyl N-alkylthiocarbamates as nematocides.

SUMMARY OF THE INVENTION

S-p-Methoxyphenyl N-2,3-dibromopropylthiolcarbamate systemically control nematodes, that is when it is applied to a plant part, such as the foliage, S-p-methoxyphenyl N-2,3-dibromopropylthiolcarbamate or a metabolite of it is translocated through the plant to the effected area, e.g., the roots, to control the nematodes' deleterious effect upon the plant. It is effective against the Meloidogyne species; especially, Meloidogyne incognita.

It is also effective to protect plants against foliar fungus disease caused by fungus of the genera Puccinia and Phytophthorans, when an effective amount of S-p-methoxyphenyl N-2,3-dibromopropylthiolcarbamate is applied to the foliage of the plant prior to infection of the plant by the fungus. This protectant control is particularly effective for the fungus species, *Phytophthorans infestans* and *Puccinia rubigo-vera*.

DESCRIPTION OF THE PREFERRED EMBODIMENTS

S-p-Methoxyphenyl N-2,3-dibromopropylthiolcarbamate is occasionally referred to as S-4-methoxyphenyl N-2,3-dibromopropylthiolcarbamate, or S-4-methoxyphenyl N-2,3-dibromopropylthiocarbamate.

Example I illustrates one method of synthesizing it.

EXAMPLE I

SYNTHESIS OF S-p-METHOXYPHENYL N-2,3-DIBROMOPROPYLTHIOLCARBAMATE

A solution of p-methoxybenzenethiol (14.0 grams, 0.1 mole) and triethylamine (1-2 drops) in 50 milliliters of anhydrous ethylether was placed into a 250 milliliter, three-necked flask. This flask was equipped with a power driven Trubore glass stirrer having a Teflon blade, an addition funnel, a Claisen type adapter fitted with a reflux condenser and thermometer. A heating mantle was placed around the flask. Allyl isocyanate (8.7 grams, 0.105 mole) was placed in the addition funnel, and added drop wise to the stirred ethylether solution over a 10 minute period. After the addition, the reaction mixture was refluxed for 2 hours; the solvent (ether) was evaporated, and the crude product remaining was recrystallized from benzene to produce 9.1 grams of white crystals having a melting point of 67°-70° Centigrade, (S-p-methoxyphenyl N-allylthiolcarbamate).

Some of these white crystals S-p-methoxyphenyl N-allylthiolcarbamate (4.4 grams, 0.020 mole) were dissolved in 150 milliliters of carbon tetrachloride and the solution was cooled to approximately 0 degrees Centigrade. A solution of bromine (3.2 grams, 0.020 mole) in 35 milliliters of carbon tetrachloride was slowly added, over an 80 minute period, to the stirred, cooled solution of S-p-methoxyphenyl N- allylthiolcarbamate. After the addition was completed, the reaction mixture was warmed to room temperature. It was washed with 75 milliliters of a 10 weight percent solution of aqueous sodium bisulfite, then with 100 milliliters of water, and dried with sodium sulfate ($Na_2SO_4$). The solvent was removed by vacuum to give 5.1 grams (67 percent yield) of a viscous, clear, colorless liquid which crystallized. This crystalline material was collected by filtration. The bulk of the crystalline material (98 percent) was dissolved in carbon tetrachloride, 100 millititers, and recrystallized therefrom using the remaining crystalline material as seed crystals. A white crystalline material (2.4 grams of s-p-methoxyphenyl N-2,3-dibromopropylthiolcarbamate) was obtained which had a melting point of 79°-83° Centigrade. This crystalline material had an IR spectra with an NH band at 3300 $cm^{-1}$ and a C=O band at 1655 $cm^{-1}$.

Analysis — $C_{11}H_{13}Br_2NO_2S$:

Calculated — C, 34.48; H, 3.42; N, 3.66.

Found — C, 34.78 ± .05; H, 3.28 ± .08; N, 3.49 ± .02.

In lieu of triethylamine, other tertiary amines such as trimethylamine or other proton acceptors such as dimethylaniline, tributylamine, or N-methylmorpholine may be used.

In the synthesis of the intermediate S-p-methoxyphenyl N-allyl- thiolcarbomate, other inert solvents which dissolve the reactants and products, and which are easily removed from the products by evaporation, drying, filtering, or washing, and which have a boiling point appropriate to the reaction temperatures may be used in lieu of ethylether. Examples are methylethylether, methylpropylether, hexane, and benzene. The reaction temperature may vary from 0° C. to the boiling point of the refluxing mixture. Preferably the reaction temperature range is from 0° C. to 50° C.

Bromination may also be accomplished by bubbling bromine gas into a solution containing the intermediate S-p-methoxyphenyl N-allyl- thiolcarbamate. The bromination reaction solvent is one which is readily removed from the product, dissolves the bromine, reactant or product and has a boiling point appropriate to the bromination reaction temperature. Examples of such solvents are carbon tetrachloride, Freons, $CCl_3Br$, and $CCl_2Br_2$. The bromination reaction temperature may vary from 0.° C, to +50° C.

As an alternative synthesis, 2,3-dibromopropylisocyanate could be used in lieu of allylisocyanate to form S-p-methoxyphenyl N-2,3-dibromopropylthiolcarbamate. The allylisocyanate may be brominated to 2,3-dibromopropylisocyanate prior to reacting with the S-p-methoxyphenylthiol.

Removal of the solvents, and reactants or other impurities from the S-p-methoxyhenyl N-2,3-dibromopropylthiolcarbamate is not necessary except insofar as they interfere with the intended use of the compound; such as for systemic nematocidal control. All conventional purification techniques such as recrystallization from solvents, fractional crystallization, washing with one or more solvents, followed by evaporation of the solvents, filtration from the solvents, or their equivalents may be used.

Other routes may be used to synthesize S-p-methoxyphenyl N- 2,3-dibromopropylcarbamate. For example, S-p-methoxyphenylthiol- chloroformate may be reacted with allylamine in an inert solvent mentioned herein in the presence of an acid acceptor at temperatures from 15° to 100° C., to form the S-p-methoxyphenyl N-allylthiolcarbamate which is then brominated. Alternatively, 2,3-bromopropylamine may be substituted for allylamine.

In another method, p-methoxyphenylthiol may be reacted with phosgene to form p-methoxyphenyl thiochloroformate according to the process set forth in U.S. Pat. No. 3,165,544, and this is reacted with allylamine or 2,3-dibromopropylamine as mentioned herein.

Alternatively, allylamine or 2,3-dibromopropylamine could be reacted with phosgene to form allylcarbamoyl chloride or 2,3-dibromopropylcarbamoyl chloride. These carbamoyl chlorides are then reacted with p-methoxyphenylthiol in an inert solvent, mentioned herein, containing an acid acceptor, mentioned herein, to form the thiolcarbamate. The p- methoxyphenyl N-allylthiolcarbamate is then brominated to form p-methoxyphenyl N-2,3-dibromopropylthiolcarbamate.

EXAMPLES II–XII

These examples illustrate systemic control of the deleterious effect of nematodes upon plants, particularly, those growing in soil infested with nematodes.

The following examples illustrate the ability of this compound to control the adverse effect of nematodes on plants by application to the foliage of a plant. It achieves this without harm to the plant, e.g., without phytotoxic, or herbicidal effects upon the plant.

The test procedure for these examples used a stock acetone solution consisting of 99.75 weight percent of acetone, 0.20 percent sorbitan trioleate (Span 85) and 0.05 percent sorbitan monooleate polyoxyalkylene derivative (Tween 80). The test compound was dissolved in an aliquot of the stock solution, and deionized water was added to form the desired concentration for spraying. For example, 1200 mg. of S-p-methoxyphenyl N-2,3-dibromopropylthiolcarbamate was dissolved in 80 grams of the stock acetone solution, and this solution was diluted to 1000 grams, to form a spray solution containing 1200 ppm of S-p-methoxyphenyl N-2,3-dibromopropylthiolcarbamate.

Bonny Best tomato plants were grown from seedlings for four or five weeks in sterile soil until their height was 6 to 8 inches, and the plants had at least three fully expanded leaves (usually more).

The growing tomato plants were separated into two groups, those for spraying (treated) and the control. The treated plants were passed through a spraying machine which sprayed them with the previously prepared test solution. The control group was not sprayed.

The solution containing S-p-methoxyphenyl N-2,3-dibromopropylthiolcarbamate was applied as a spray by passing a tray of pots containing tomato plants, under a sprayer equipped with a Tee-Jet 8001 E spray nozzle tip and operating in the range of 35–40 pounds per square inch of pressure. The pot containing the plant was loaded within a tray which was placed on a conveyor belt moving at about 0.0625 mph (5.49 feet per minute). When the tray passed under the spray head, it tripped a microswitch which operated the sprayer. The spray was applied to the dripping point. The amount of compound within the solvent was adjusted to give the required application rate expressed as parts per million (ppm) for the active ingredient per 30 milliliter of solution or pounds of active ingredient per 200 gallons per surface acre (lbs, ai/200 gal/acre) of soil. In these examples the sprayer sprayed 30 milliliters of solution per replicate. The sprayed plants were dried; then they and the control plants were transferred into soil infested with root-knot nematodes (*Meloidogyne incognita*), and grown under geeenhouse conditions.

Both the sprayed (treated) and control plants were uprooted 4 weeks after being transferred to the infested soil, and their roots were examined for root-knots which were counted in accordance with the method of W. M. Zeck. *Pflanzenschutz —Nachrichten*, Vol. 24, pages 141-144 (1971). The control is also rated according to the Zeck index. The root-knot counts were related to percent control by the following formula:

% control =
$$100\% \times \frac{\text{No. of root-Knots in control-No. of root-knots treated}}{\text{No. of root-knots in control}}$$

Vydate (Dupont 1410 - methyl N',N'-dimethyl-N-[(methylcarbamoyl)oxy]-1-thiooxamimidate) a systemic nematocide known to be effective against the root-knot nematodes was also tested at the same concentration as the test compound and under the same conditions, as an internal check in some example. Treated plants were also observed for evidence of damage by the applied test compound. This is reported on a scale of 0 to 10, with zero indicating no effect and ten indicating complete kill.

Five replicates per concentration of the test compound are made and an average percent control is determined based on these five replicates. Each replicate is based on 2 plants. An average value of 10 or higher indicates systemic control.

The test results are given in Table 1. Column 1 gives the example number; column 2 gives the concentration (conc.) of compound used expressed as parts per million (ppm); column 3 gives the individual percent control per replicate for the S-p-methoxyphenyl N-2,3-dibromopropylthiolcarbamate form Example I; column 4 gives the individual percent control per replicate of Vydate; and column 5 gives the average Zeck index rating of the control plants.

The test results indicate that S-p-methoxyphenyl N-2,3-dibromopropylthiolcarbamate systemically controls the deleterious effects of root-knot nematodes upon plants.

TABLE 1

SYSTEMIC CONTROL OF ROOT-KNOT NEMATODE, (*Meloidogyne incognita*) UPON TOMATO PLANTS

| Example No. | Conc. ppm (1) | S-p-methoxyphenyl N-2,3-dibromopropylthiolcarbamate (Example I) Percent Control Replicate | | | | | Vydate Percent Control-Replicate | | | | | Zeck Index Rating |
|---|---|---|---|---|---|---|---|---|---|---|---|---|
| | | 1 | 2 | 3 | 4 | 5 | 1 | 2 | 3 | 4 | 5 | |
| II | 4000 | 25 | 100 | 75 | 75 | 100 | 100 | 100 | 100 | 100 | 100 | 4.0 |
| III | 2000 | 25 | 100 | 75 | 50 | 25 | 100 | 100 | 100 | 100 | 75 | 4.0 |
| IV | 1000 | 50 | 75 | 75 | 75 | 75 | 100 | 100 | 75 | 75 | 75 | 4.0 |
| V | 500 | 75 | 25 | 100 | 75 | 75 | 75 | 100 | 50 | 75 | 75 | 4.0 |
| VI* | 4000 | 25 | 40 | 40 | 55 | 40 | Not | Tested | | | | 6.7 |
| VII | 2000 | 25 | 40 | 25 | 25 | 55 | '' | '' | | | | 6.7 |
| VIII | 1000 | 0 | 0 | 0 | 0 | 10 | '' | '' | | | | 6.7 |
| IX | 500 | 0 | 10 | 0 | 0 | 0 | '' | '' | | | | 6.7 |
| X | 500 | 86 | 86 | 86 | 86 | 58 | 44 | 44 | 72 | 72 | 86 | **7.1 |
| XI | 50 | 58 | 44 | 86 | 44 | 72 | 44 | 15 | 44 | 44 | 15 | **7.1 |
| XII | 5 | 58 | 44 | 72 | 44 | 30 | 15 | 15 | 0 | 0 | 0 | **7.1 |

*Plants showed burn effects at this concentration
**Control plants had an average of 266 surface knots per plant based on 12 replicates. At high Zeck index ratings, only the knots on the outer roots (surface knots) are counted.

The deleterious effects of other Meloidogyne species may be systemically controlled by S-p-methoxyphenyl N2,3-dibromopropylthiolcarbamate. The species *Meloidogyne exigua* (Cofee Root-knot Nematode), *Meloidogyne arenaria* (Peanut Root-knot Nematode), *Meloidogyne hapla* (Northern Root-knot Nematode), and Citrus root Nematode are examples of other Meloidogyne species which may be controlled. *Ditylonchus destructor* (Potato Rot Nematode) is another nematode which may be controlled by this compound. The *Meloidogyne incognita* nematode in particular is systemically controlled by the compound.

Other species of nematodes may be controlled by applications other than systemic foliage contact, for example, by supplying the compound to the soil, or by dipping the bulbs in solutions. Some examples of these other nematodes are:

*Aphelenchoides species:* Bud and Leaf Nematodes
*Anguina tritici;* Wheat Nematode
*Anguina agrostis;* Grass Nematode
*Belonolaimus species;* Sting Nematodes
*Criconemoides species;* Ring Nematodes
*Ditylonchus dipsaci;* Stem and Bulb Nematode
*Ditylonchus angustus;* Rich Nematode
*Dolichodorus heterocephalus;* Awl Nematode
*Helicotylenchus species;* Spiral Nematodes
*Heterodera rostochiensis;* Golden Nematode
*Heterodera tabacum;* Tobacco Cyst Nematode
*Heterodera schachtii;* Sugar Beet Nematode
*Heterodera carotae;* Carrot Root Nematode
*Heterodera gottingiana;* Pea Root Nematode
*Heterodera glycines;* Soybean Cyst Nematode
*Hoplolaimus species;* Lance Nematodes
*Pratylenchus brachyurus;* Smooth-headed Lesion Nematode
*Pratylenchus species;* Meadow Nematodes
*Pratylenchus musicola;* Banana Nematode
*Pratylenchus zeae;* Corn Nematode
*Radopholus similis;* Burrowing Nematode
*Rotylenchus reniformis;* Kidney-shaped Nematode
*Trichodorus species;* Stubby-root Nematodes
*Tylenchorhynchus claytoni;* Tobacco Stunt Nematode
*Xiphinema specis;* Dagger Nematodes S-p-methoxyphenyl N-2,3-dibromopropylthiolcarbamate may itself be applied directly to the infested area where the deleterious effects of the nematodes are to be controlled. It is, however, preferable to use suitable agricultural formulations which contain other ingredients which enhance application of this compound. These agricultural formulations will generally comprise from 5 percent to 95 percent by weight of S-p-methoxyphenyl N-2,3-dibromopropylthiolcarbamate, and either from 1 percent to 95 percent by weight of an agricultural diluent, or from 1 percent to 20 percent by weight of a surface active agent and other ingredients reguired to produce wettable powders, dusts, solutions, emulsifiable concentrates, granules and the like.

Wettable powders will contain from 25 to 80 percent active ingredients, from 0.1 percent to 5.0 percent wetters and dispersants with the balance consisting of inorganic absorptive diluents.

Since the compound is a solid, it may be melted and sprayed upon the absorptive diluents of attapulgite clay, synthetic fine silica, and synthetic calcium and sodium aluminosilicates, or other solid insecticides, or foliar fungicides mentioned herein. It can be dissolved in a solvent and sprayed upon these solid diluents, and then the solvent is evaporated off.

Emulsifiable oils will contain from 20 percent to 97 percent active ingredient, from 3.0 to 10.0 percent of an emulsifying agent, and may also contain from 1 percent to 77 percent water-immiscible solvent such as xylene or alkylated naphthalene.

Granules will contain from 5 percent to 25 percent active ingredient, and may also contain from 1 percent to 20 percent of a surfactant extended upon a granular base such as vermiculite or granular attapulgite. Granules produced by extrusion or tumbling will contain like amounts of active ingredient and surfactant.

For the control of a wider range of crop-pests and diseases it is sometimes desirable to combine S-p-methoxyphenyl N-2,3-dibromo- propylthiolcarbamate with from 0.05 to 4 parts by weight of insecticides and fungicides, etc., known to be effective against crop-pests and diseases in concentrated premix or during the application step for foliar applications. Examples of other pesticides are: granules of stable metal azide-metal salt formulations disclosed in assignee's copending application, Ser. No. 624,357, filed Oct. 21, 1975. Sevin (1-naphthyl-N-methylcarbamate), Chlorobenzilate (ethyl 4,4'-dichlorobenzilate), Guthion (0,0-diethyl-S-[4-oxo-1,2,3-benzotriazin-3(4H)-ylmethyl]phosphorodithioate), Disyston (0,0-diethyl-S-[2-(ethylthio)ethyl]-phosphorodithioate, Maneb (manganous ethylene bisdithiocarbamate), Karathane (a mixture of 2-(1-methylheptyl)-4,6-dinitrophenylcrotonate, 2-(1-ethylhexyl)4,6-dinitrophenylcrotonate, 2-(1-propylpentyl) 4,6-dinitrophenylcrotonate, 4,6-dinitro-2-octylphenylcrotonate, 4-(1ethylhexyl)2,6-dinitrophenylcrotonate, 4-(1-methylheptyl)2,6-dinitrophenylcrotonate, 4-(1-propylpentyl)2,6-dinitrophenylcrotonate, and nitrooctylphenols (principally dinitro)), Blasticidin (blasticindin-S-benzyl-aminobenzensulfonate), Benlate (methyl 1-(butylcarbamoyl)-2-benzimida- zolecarbamate, or Plantvax (5,6-dihydro-2-methyl-1,4-oxathiin-3-carboxanilide- 4,4-dioxide).

In some instances it is also desirable to include special purpose additives which will inhibit corrosion, reduce foaming, reduce caking or increase flocculation.

S-p-methoxyphenyl N-2,3-dibromopropylthiolcarbamate, also exhibits foliar fungicidal activity against pathogenic fungus.

In test procedures similar to that described for systemic control of nematodes, wherein plants are inocculated with the fungus, before application, and after application of S-p-methoxyphenyl N-2,3-dibromopropylthiolcarbamate, it was discovered that the compound that the compound had protectant activity (that is its application to the plant prior to inocculation or on contact with the fungus, protects the plant) against Late Blight of Tomatoes (*Phytophthorans infestans*), and Lef Rust of Wheat (*Puccinia rubigo-vera*9.

APPLICATION

S-p-methoxyphenyl N-2,3-dibromopropylthiolcabamate, when used to control the deleterious effects of nematodes upon plants and plant parts, is applied in an effective amount as a suitable agricultural formulation within the vicinity of the infested area where the deleterious effects of the nematodes are to be controlled.

The phrase "to control the deleterious effects of nematodes upon plants and plant parts" means that the adverse effects of the nematodes upon the plants are reduced in intensity. This control may be direct control or systemic control which results from one mechanism or combination of several mechanisms; such as (a) direct killing of the nematodes; (b) repelling of the nematodes; or (c) rapid healing of the plant attacked by the namatode. In systemic control, S-p-methoxyphenyl N-2,3-dibromopropylthiolcarbamate is applied within the vicinity of the infested area, e.g., to the foliage of the plant which has its roots infested by root nematodes, rather than directly to the infested area, e.g., the plant roots itself. Systemic control may result from a single mechansim or from a combination of mechanisms. It may result from a translocation of S-p-methoxyphenyl N-2,3-dibromopropylthiolcarbamate, (or a metabolite thereof) from its application site (e.g., the foliage), to the area deleteriously effected by the nematodes (e.g., the roots, or the center portion of the stem) where it controls the deleterious effect by (a) killing the nematodes; (b) repelling the nematodes; or (c) by healing the plant; or from translocation into the plant enzyme system which it induces the enzyme system to produce chemicals which (a) kill the nematodes or (b) repel them, or (c) which promotes rapid healing of the plant. Systemic control may also result from a translocation of S-p-methoxyphenyl N-2,3-dibromopropylthiolcarbamate (or a metabolite of it) from its application site (foliage) through the plant to outside of the area (the roots) deleteriously affected by nematodes where it provides a protective shield against the nematodes; such as a root coating which repels or kills nematodes feeding upon this area of the plant.

The effective amount varies with the particular nematode involved, the application method used, e.g., systemic, soil incorporation, or dusting with a powder; the type of formulation utilized, the plant species to be protected, and local conditions such as temperature, humidity, moisture content of the soil, nature of the soil and the like. Since many factors are involved, different rates of application are selected for best results depending upon these specific conditions.

The phrase "applied to the parts of the plant" refers to any method of application as by spraying or dusting the part of the plant which is above-ground, such as its foliage, bark or stem; or plant parts which are underground, such as bulbs, canes, tubers, or roots with S-p-methoxyphenyl N-2,3-dibromopropylthiolcarbamate.

For systemic control, S-p-methoxyphenyl N-2,3-dibromopropylthiolcarbamate is applied preferably as a spray to the foliage of plants, particularly, to plants growing in soil infested with root-knot nematodes of the Meloidogyne species, particularly *meloidogyne incognita*.

For other nematodes, it is possible to apply the compound by dipping the canes, or tubers, or bulbs effected by nematodes which attack these parts of the plants into solutions containing S-p-methoxyphenyl N-2,3-dibromopropylthiolcarbamate, or by dusting these parts with granules or powders containing the compound.

The effective amount of S-p-methoxyphenyl N-2,3-dibromopropylthilcarbamate for systemic control of Meloidogyne species, particularly *Meloidogyne incognita*, is a solution containing from 5 ppm to the maximum amount tolerated by the plants applied as a spray to the dripping point. In general it is from 5 ppm to 4,000 ppm, normally from 5 ppm to 500 ppm, and preferably from 5 ppm to 200 ppm.

These same amounts of S-p-methoxyphenyl N-2,3-dibromopropylthiolcarbamates are applied when the compound is used in combination with insecticides such as Sevin, Chlorobenzilate, Guthion, Disyston, or foliar fungicides such as Maneb, Karathane, Blasticidin, Benlate, or Plantvax. The amount of these other insecticides or fungicides will be in accordance with the label instructions disclosed in technical literature given with these known commercial compounds. In some cases, better control of the deleterious effects of nematodes is obtained when S-p- methoxyphenyl N-2,3-dibromopropylthiolcarbamate is used in combination with the aforementioned insecticides and foliar fungicides.

Other applications methods may include spraying above-ground parts such as stems, leaves and buds in which nematodes are already present or where later attack is expected. Examples of these other applications are: dipping or soaking the reproductive parts in an aqueous suspension, solution or emulsion of an active ingredient; dusting above-ground parts or reproductive parts with a dust composition of an active ingredient, or immersing the root system to disinfect the plant or to provide protection against subsequent nematode invasion. The reproductive parts may be seeds, cane pieces, and bulbs which are infested or are to be planted in infested soil.

The effective amount of S-p-methoxyphenyl N-2,3-dibromopropylthiolcarbamate for applying directly to the infested area in which nematodes are present, or directly to areas which may become infested with nematodes is the same amount mentioned herein. This amount may also be from 20 to 100 pounds per acre, but preferably from 50 to 75 pounds per acre. Of course, higher rates may also be used.

For a more effective control of the deleterious effects of root-knot nematodes upon plants, particularly Meloidogyne species, especially *Meloidogyne incognita*, it is preferably to apply a contact nematocide such as sodium or potassium azide, Nemagon, Nemacur, or S-p-methoxyphenyl N,N-bis(2,3-dibromopropyl)thiolcarbamate (see assignee's copending application, Ser. No. 631,802, filed Nov. 13, 1975) to the soil before planting the crops so as to reduce the number of pathogenic nematodes contained therein, and then after planting the crop to maintain control of the deleterious effects of nematodes on the plants by applying an effective amount of S-p-methoxyphenyl N-2,3-dibromopropylthiolcarbamate to systemically control the deleterious effects of the nematodes.

It is best to remove as much of the pathogenic pests from the soil, by applying sodium or potassium azides as mentioned herein, or Nemagon (1,2-dibromo-3-chloropropane), Nemacur (0-phenyl N,N'-dimethyl- phosphorodiamidate), as well as soil fungicides and insecticides, such as: Captan (cis-N-(trichloromethyl)thio)-4-cyclohexene-1,2-dicarboximide), Dexon (p-dimethylaminobenzenediazo sodium sulfate), PCNB (pentachloronitrobezene), Furadan (2,3-dihydro-2,2-dimethyl-7-benzofuranyl- methylcarbamate), Mocap (0-ethyl S,S-dipropylphosphorodithioate), or Temik (2-methyl-2)methylthio)propionaldehyde 0-(methylcarbamoyl)oxime), prior to planting the crops followed by one or more applications of S-p- methoxyphenyl N-2,3-dibromopropylthiolcarbamate to the plant's foliage during plant growth to maintain better systemic control of the deleterious effects of nematodes.

S-p-methoxyphenyl N-2,3-dibromopropylthilcarbamate is effective to control the deleterious effect of nematodes particularly Meloidogyne species and in particular *Meloidogyne incognita* upon plants effected by these nematodes; especially plants such as ornamentals, banana, avocado, sugar cane, pineapple, tobacco, citrus, soybeans, coffee, peanuts, corn, cucumbers, or garden crops such as sweet potato, tomato, carrot, celery, sugar beets, potato, etc.

In application against foliar fungicides, such as those caused by fungus of th Puccinia genera, in particular *Puccinia rubigo-vera, Puccinia carthami,* and those of the genera Phytophthorans and particularly *Phytophthorans infestans,* an effective amount of S-p-methoxyphenyl N-2,3-dibromopropylthiolcarbamate is applied to the foliage of the plants prior to infection of the plants with the said diseases to control these diseases.

The effective concentration of the solution applied to the foliage to the dripping point varies from 100 ppm to the maximum tolerated by the foliage of plants such as safflowers, wheat, tomato, or ornamentals such as snap dragons, but generally the effective amount is from 100 ppm to 500 ppm of S-p-methoxyphenyl N-2,3-dibromopropylthiolcarbamate.

The following example illustrates a suitable emulsifiable concentrate formulation for dilution in water for spraying plants, particularly, plant foliage or for application to other plant parts as herein mentioned. In this emulsifiable concentrate formulation, the percentages are weight percent.

EXAMPLE XIII

| Emulsifiable Concentrate Formulation | |
|---|---|
| S-p-methoxyphenyl N-2,3-dibromopropylthiolcarbamate | 13% |
| Xylene | 41% |
| Isophorone | 41% |
| Atlox®3404* | 1% |
| Atlox®3403 F* | 4% |

*Commercial emulsifier for agricultural pesticides manufactured by Atlas Powder Co., Wilmington, Delaware, and registered with the U.S. Food and Drug Administration.

The concentration of S-p-methoxyphenyl N-2,3-dibromopropylthiolcarbamate in the emulsifiable concentrate may vary from 5 to 15 weight percent, the xylene may vary from 35 to 45 weight percent, isophorone may vary from 38 to 45 weight percent, Atlox (R)

3404 may vary from 0.5 to 0.3 weight percent, and Atlox (R) 3403 F may vary from 3 to 6 weight percent.

While the invention has been described with reference to specific details of certain illustrative embodiments, it is not intended that it shall be limited thereby except insofar as such details appear in the accompanying claims.

I claim:

1. S-p-methoxyphenyl N-2,3-dibromopropylthiolcarbamate.

2. A method of controlling the deleterious effects of plant pathogenic nematodes upon plants and plant parts which comprises:
   applying an effective amount of S-p-methoxyphenyl N-2,3- dibromopropylthiolcarbamate to the area deleteriously effected by said nematodes to control said deleterious effects of the nematodes.

3. A method of systemically controlling the deleterious effects of plant pathogenic nematodes upon plants which comprises:
   applying an effective amount of S-p-methoxyphenyl N-2,3- dibromopropylthiolcarbamate to the aboveground parts of the plant to control the deleterious effects of said nematodes upon the plant.

4. The method as recited in claim 3, wherein said nematode is a nematode causing root-knots.

5. The method as recited in claim 4, wherein the plant is selected from the group consisting of an ornamental, banana, avocado, sugar cane, pineapple, tobacco, citrus, soybean, coffee, peanut, corn, cucumber, sweet potato, potato, tomato, celery, and sugar beet.

6. The method as recited in claim 5, wherein the nematode is Meloidogyne species.

7. The method as recited in claim 6, wherein S-p-methoxyphenyl N-2,3-dibromopropylthiolcarbamate is applied to the foliage of said plants.

8. The method as recited in claim 7, wherein the nematode is selected from the group consisting of *Meloidogyne incognita* and *Meloidogyne hapla*.

9. A method of controlling the deleterious effects of plant pathogenic nematodes upon plants to be grown in soil infested with nematodes, which comprises:
   applying an effective amount of a contact nematocide to said soil prior to planting said plants to reduce the number of pathogenic nematodes contained therein, planting said plant in the treated soil, and
   applying an effective amount of S-p-methoxyphenyl N-2,3- dibromopropylthiolcarbamate to the upper parts of the plant to control said deleterious effects of pathogenic nematodes upon said plant.

10. The method of claim 9, wherein the plant is selected from the group consisting of ornamentals, banana, avocado, sugar cane, pineapple, tobacco, citrus, soybean, coffee, peanut, corn, cucumber, sweet potato, potato, tomato, carrot, celery, and sugar beet.

11. The method as recited in claim 10, wherein the pathogenic nematode is a nematode causing root-knots.

12. The method as recited in claim 11, wherein the upper part of the plant is the foliage of the plant.

13. The method as recited in claim 12, wherein the pathogenic nematode is a species of the genera Meloidogyne.

14. The method as recited in claim 12, wherein the pathogenic nematode is selected from the group consisting of *Meloidogyne incognita* and *Meloidogyne hapla*.

* * * * *